United States Patent [19]
Brahler

[11] Patent Number: 5,380,202
[45] Date of Patent: Jan. 10, 1995

[54] DENTAL PROPHY CUP

[75] Inventor: George R. Brahler, Lawrence, Kans.

[73] Assignee: Brahler Products, Inc., Lawrence, Kans.

[21] Appl. No.: 186,994

[22] Filed: Jan. 27, 1994

[51] Int. Cl.⁶ ................................................ A61C 3/06
[52] U.S. Cl. ..................................................... 433/166
[58] Field of Search ................................. 433/125, 166

[56] References Cited

U.S. PATENT DOCUMENTS

| | | | |
|---|---|---|---|
| 2,017,881 | 10/1935 | Wiseman | 433/166 |
| 2,226,145 | 12/1940 | Smith | 433/166 |
| 2,738,528 | 3/1956 | Fridge, Sr. | 433/166 |
| 3,599,333 | 8/1971 | Muhler | 433/166 |
| 4,259,071 | 3/1981 | Warden et al. | 433/166 |
| 4,753,594 | 6/1988 | Croll | 433/166 |

*Primary Examiner*—Cary E. O'Connor
*Attorney, Agent, or Firm*—Hovey, Williams, Timmons & Collins

[57] ABSTRACT

A disposable dental prophy cup designed to be coupled with a dental prophy angle for simultaneously cleansing both the surface of teeth and the surrounding tissue and gingival crevice. The dental prophy cup includes a concentric sidewall including a coupling orifice for coupling the prophy cup with the output member of a dental prophy cup, wherein the rotation of the prophy angle output member causes the prophy cup to rotate, and cleansing ribs attached to the outer surface of the sidewall for cleansing the tissue of the gingival crevice of a tooth when the prophy cup is rotated by the prophy angle output member.

8 Claims, 2 Drawing Sheets

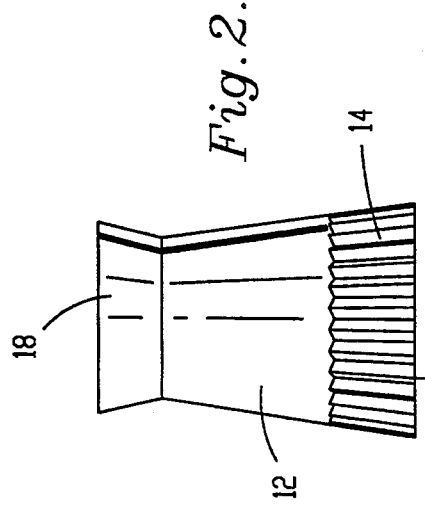
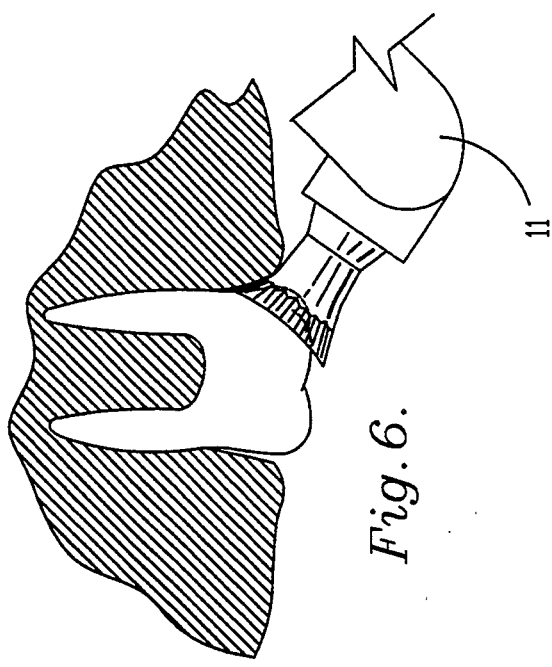
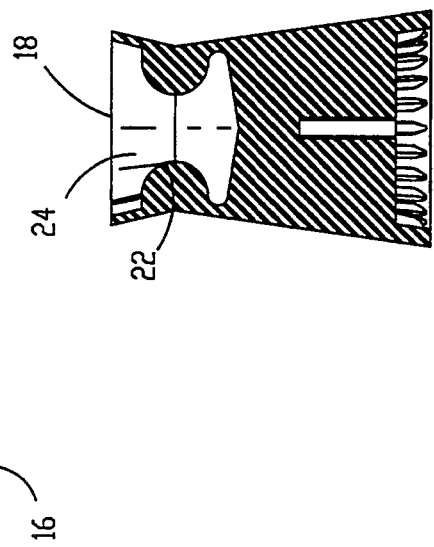
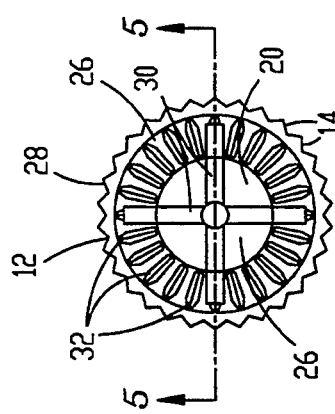
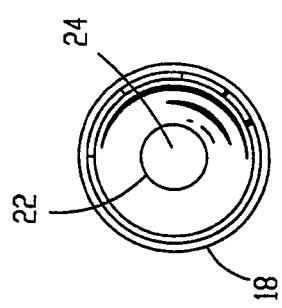

DENTAL PROPHY CUP

BACKGROUND OF THE INVENTION

1. Field of the Invention

The present invention is concerned with the field of dentistry and specifically with the field of disposable dental prophy cups designed to be coupled with dental prophy angles used for dental prophylaxis. The disposable dental prophy cup and prophy angle are used to clean both the surface and the surrounding tissue and gingival crevice of a patient's teeth.

2. Description of the Prior Art

Disposable dental prophy cups attached to disposable prophy angles for use in cleaning a patient's teeth are known in the field of dentistry. These prior art prophy cups are generally fabricated of a flexible compound and are coupled to the output shaft of a prophy angle, wherein the rotation of the prophy angle output shaft causes the prophy cup to rotate. In use, a dentist or assistant applies a cleaning compound to the surface of the prophy cup and cleans and polishes a patient's teeth by applying the rotating prophy cup to the patient's teeth and gums.

Prior art prophy cups often include ribs or webs extending inwardly from the cup's inner wall to mechanically remove plaque, stains, and other debris from the surface of the patient's teeth. While these internally extending ribs or webs effectively clean the surface of the teeth, they do not provide for cleansing of the gum and gingival crevice surrounding the teeth. The gingiva is the part of the gum tissue encircling the necks of teeth and the gingival crevice is the portion of the gingiva slightly below the surface of the gum line at the base of an erupted tooth. The dental profession has recently recognized that effective dental disease control requires removal of plaque, stain and microorganisms from both the teeth surface and the gums and gingival crevice surrounding the teeth. Thus, the prior art points out the need for an improved prophy cup with cleansing means for cleansing the gum and tissue of the gingival crevice of a tooth when the prophy cup is applied to a tooth and rotated by a prophy angle.

SUMMARY OF THE INVENTION

The present invention overcomes the problems outlined above and provides a distinct advance in the field of dental prophy cups. More particularly, the prophy cup of the present invention provides a cleansing structure which simultaneously cleans both the surface of the teeth and the surrounding tissue and gingival crevice.

The preferred prophy cup includes a concentric sidewall presenting a head end and a shank end and with coupling means for coupling the prophy cup with the output member of a dental prophy cup. Once coupled, rotation of the prophy angle output member causes the prophy cup to rotate along an axis extending longitudinally along the center of the concentric sidewall.

The preferred prophy cup also includes cleansing means attached to the outer surface of the sidewall for cleansing the surrounding tissue and gingival crevice of a tooth when the prophy cup is rotated by the prophy angle output member. In particularly preferred forms the prophy cup also includes a plurality of crossed vanes and spaced internal ribs extending inwardly from the sidewall inner surface for cleansing the surface of a tooth while the prophy cup is in use.

BRIEF DESCRIPTION OF THE DRAWINGS

FIG. 2 is a side elevational view of the prophy cup;

FIG. 3 is a bottom view of the shank end of the prophy cup;

FIG. 4 is a top view of the head end of the prophy cup;

FIG. 5 is a side sectional view of FIG. 2 showing the coupling means for coupling the prophy cup to the prophy angle; and FIG. 6 is an application view showing the prophy cup cleansing both the surface of a tooth and the surrounding gingival crevice and gum.

DETAILED DESCRIPTION OF THE PREFERRED EMBODIMENTS

Figure 1:
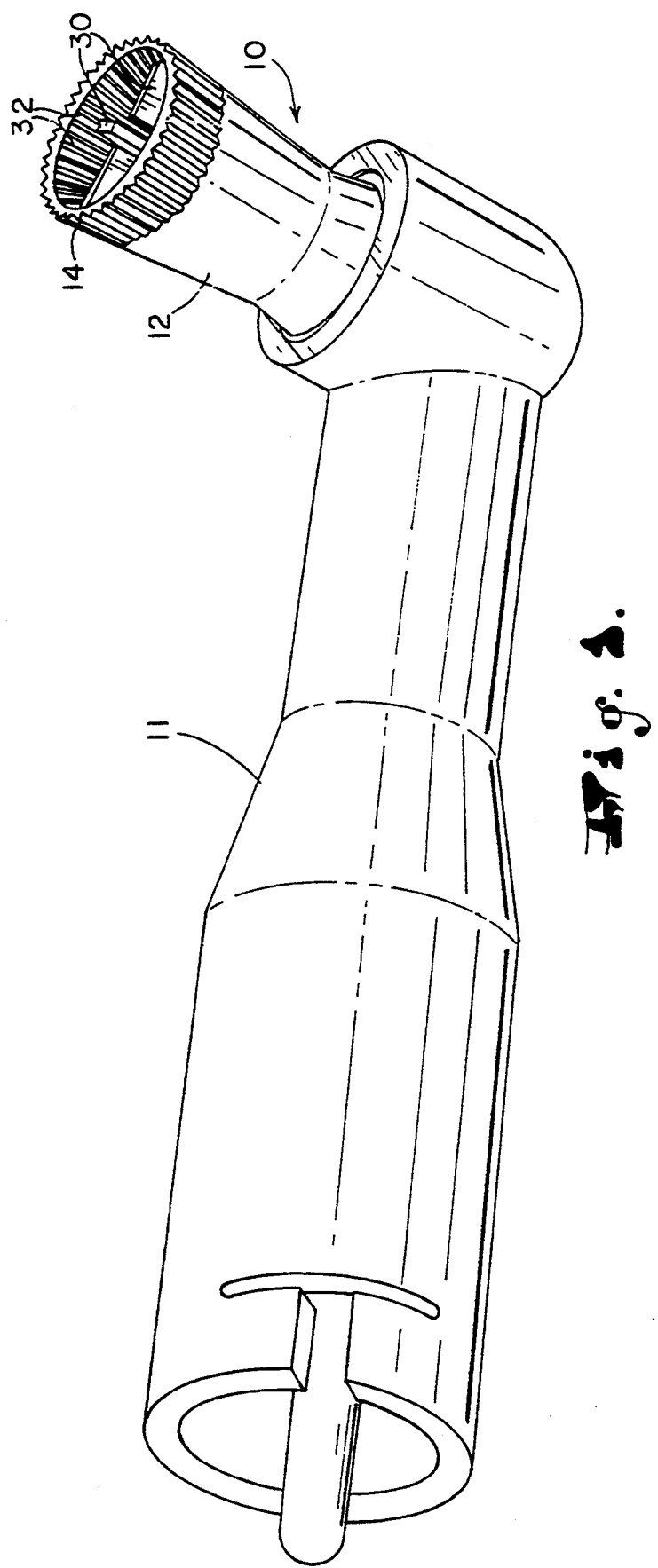
FIG. 1 is a perspective view of the preferred deposable prophy cup shown attached to a typical prophy angle.

Turning now to the drawings, and particularly FIG. 1, prophy cup 10 broadly includes concentric sidewall 12 and external cleansing ribs 14. Prophy cup 10 is designed to be coupled with a prophy angle 11 for cleansing and polishing the teeth and surrounding tissue of a patient. The components of prophy cup 10 are preferably composed of a pliable rubber or elastic compound and are integrally molded to form a unitary structure.

Concentric sidewall 12 forms the outer shell of prophy cup 10 and is essentially molded in the shape of a truncated cone. As illustrated in FIG. 2, concentric sidewall 12 presents a head end 16 and a shank end 18. Head end 16 is configured for contacting a patient's teeth and surrounding tissue while shank end 18 is configured for coupling with a prophy angle. As illustrated in FIG. 4, head end 16 presents an open cavity 20 concentrically surrounded by sidewall 12. Open cavity 20 receives the surface of a tooth while prophy cup 10 is in use as illustrated in FIG. 6.

As best illustrated in FIGS. 3 and 5, shank end 18 includes circular wall 22 defining an orifice 24 for receiving and coupling with the output member of a prophy angle 11. When coupled together, rotation of the prophy angle output member (not shown) causes prophy cup 10 to rotate along an axis extending longitudinally along the center of concentric sidewall 12.

Concentric sidewall 12 of prophy cup 10 further presents an inner surface 26 and an outer surface 28. As illustrated in FIG. 4, a plurality of crossed vanes 30 extend inwardly from sidewall inner surface 26 towards open cavity 20 for cleansing the surface of a tooth while prophy cup 10 is in use. In preferred forms, crossed vanes 30 are integrally formed as part of sidewall 12. When prophy cup 10 is rotated, crossed vanes 30 provide an agitator action which dislodges plaque, debris, and microorganisms from the surface of the tooth.

Concentric sidewall 12 also includes a plurality of spaced internal ribs 32 disposed between sidewall crossed vanes 30 extending inwardly from sidewall inner surface 26 towards open cavity 20 for cleansing the surface of a tooth while prophy cup 10 is in use. In preferred forms, internal ribs 32 are integrally formed as part of sidewall 12. When prophy cup 10 is rotated, internal ribs 32 provide a friction action which dislodges plaque, debris, and microorganisms from the surface of the tooth.

External cleansing ribs 14 are attached to outer surface 28 of prophy cup 10 and provide for cleansing of a tooth's surrounding gingival crevice and gum. External ribs 14 extend outwardly from sidewall outer surface 28 and are preferably integrally molded as a part of sidewall 12. In the preferred embodiment, external cleansing ribs 14 are spaced along the entire circumference of sidewall outer surface 28 and form a continuous cleansing structure. The apex of external ribs 14 mechanically disrupt microorganisms and debris in the gingival crevice of the tooth while massaging the tissue surrounding the tooth to provide for complete cleaning of a patient's teeth and gums. As those skilled in the art will appreciate, external cleansing ribs 14 can be molded in a variety of shapes and sizes.

In use, prophy cup 10 is attached to the output member of a prophy angle for use in cleaning and polishing a patient's teeth and gums to remove plaque, stains, microorganisms and other debris. To attach prophy cup 10, orifice 24 of shank end 18 is press-fit on to the output member of prophy angle 11. Once coupled, the rotation of the prophy angle output member causes prophy cup 10 to rotate along an axis extending along the center of concentric sidewall 12.

To clean a patient's teeth and gums, a dentist or assistant applies a cleaning compound to the surface of the prophy cup and applies the rotating prophy cup to the patient's teeth and gums as illustrated in FIG. 6. Crossed vanes 30 and spaced internal ribs 32 mechanically disrupt plaque, debris or microorganisms from the surface of the tooth. Simultaneously, external ribs 14 mechanically disrupt microorganisms and debris in the gingival crevice of the tooth while massaging the tissue surrounding the tooth to provide for complete cleaning of a patient's teeth and gums.

Thus, the preferred embodiment of the disposable prophy cup described above provides a distinct advance in the field of dental prophy cups. More particularly, the prophy cup of the present invention provides a cleansing means for simultaneously cleansing both the surface of the teeth and the gum and gingival crevice surrounding the teeth.

As those skilled in the art will appreciate, the present invention encompasses many variations in the preferred embodiment described herein. For example, the exterior cleansing ribs of the invention could be replaced with any device which extends outwardly from the prophy cup outer wall and provides mechanical agitation of the gums and gingival crevice surrounding a tooth.

Having thus described the preferred embodiment of the present invention, the following is claimed as new and desired to be secured by Letters Patent:

1. A dental prophy cup for use with a dental prophy angle comprising:
   a concentric sidewall presenting a head end and a shank end, said head end presenting walls defining an open cavity concentrically surrounded by said sidewall for receiving the surface of a tooth, said shank end including coupling means for coupling said prophy cup with the output member of a dental prophy angle, wherein the rotation of said prophy angle output member causes said prophy cup to rotate about an axis extending along the center of said concentric sidewall, said sidewall further presenting an inner surface and an outer surface; and
   cleansing means on said outer surface of said sidewall for cleansing the surrounding tissue and gingival crevice of a tooth when said prophy cup is rotated by said prophy angle output member, said sidewall head end having a thin, pliable edge which easily penetrates the gingival crevice of a tooth so that said cleansing means contacts the gingival crevice, said cleansing means including a plurality of spaced external ribs integrally molded to the outer surface of said sidewall configured for cleansing and massaging the surrounding tissue and gingival crevice of a tooth while said prophy cup is in use.

2. The dental prophy cup as set forth in claim 1, said external ribs being integrally formed as part of said sidewall.

3. A dental prophy cup for use with a dental prophy angle comprising:
   a concentric sidewall presenting a head end and a shank end, said head end presenting walls defining an open cavity concentrically surrounded by said sidewall for receiving the surface of a tooth said shank end including coupling means for coupling said prophy cup with the output member of a dental prophy angle, wherein the rotation of said prophy angle output member causes said prophy cup to rotate about an axis extending along the center of said concentric sidewall, said sidewall further presenting an inner surface and an outer surface;
   cleansing means on said outer surface of said sidewall for cleansing the surrounding tissue and gingival crevice of a tooth when said prophy cup is rotated by said prophy angle output member; and
   a plurality of crossed vanes extending inwardly from said sidewall inner surface for cleansing the surface of a tooth while said prophy cup is in use.

4. The dental prophy cup as set forth in claim 3, said prophy cup further including a plurality of spaced internal ribs disposed between said sidewall crossed vanes extending inwardly from said sidewall inner surface for cleansing the surface of a tooth while said prophy cup is in use.

5. The dental prophy cup as set forth in claim 4, said internal ribs being integrally formed as part of said sidewall.

6. The dental prophy cup as set forth in claim 3, said vanes being integrally formed as part of said sidewall.

7. A dental prophy cup for use with a dental prophy angle comprising:
   a concentric sidewall presenting a head end and a shank end, said head end presenting walls defining an open cavity concentrically surrounded by said sidewall for receiving the surface of a tooth, said shank end including walls defining an orifice for receiving and coupling said prophy cup with the output member of a dental prophy cup, wherein the rotation of said prophy angle output member causes said prophy cup to rotate about an axis extending along the center of said concentric sidewall, said sidewall further presenting an inner surface and an outer surface;
   a plurality of crossed vanes extending inwardly from said sidewall inner surface for cleansing the surface of a tooth while said prophy cup is in use;
   a plurality of spaced internal ribs disposed between said sidewall crossed vanes extending inwardly from said sidewall inner surface for cleansing the surface of a tooth while said prophy cup is in use; and
   cleansing means attached to said outer surface of said sidewall for cleansing the surrounding tissue and gingival crevice of a tooth when said prophy cup is rotated by said prophy angle output member, said cleansing means including a plurality of spaced external ribs integrally molded to the outer surface of said sidewall.

8. A dental prophy cup for use with a dental prophy angle comprising:

a concentric sidewall presenting a head end and a shank end, said sidewall head end defining an open cavity for receiving the surface of a tooth, said shank end including coupling means for coupling said prophy cup with the output member of a dental prophy angle, wherein the rotation of said prophy angle output member causes said prophy cup to rotate about an axis extending along the center of said concentric sidewall, said sidewall further presenting an inner surface and an outer surface; and cleansing means mounted to and extending from said outer surface for cleansing the surrounding tissue and gingival crevice of a tooth when said prophy cup is in use, said cleansing means including a plurality of spaced outwardly extending ribs integrally molded to the outer surface of said sidewall, said external ribs being essentially triangular shaped in cross section.

* * * * *